United States Patent
Lin et al.

(10) Patent No.: US 10,918,683 B2
(45) Date of Patent: Feb. 16, 2021

(54) METHODS TO REDUCE FAT ACCUMULATION AND OXIDATIVE DAMAGE IN LIVER USING GREEN MANGO EXTRACTS AND COMPOUNDS OBTAINED THEREFROM

(71) Applicant: TCI CO., LTD., Taipei (TW)

(72) Inventors: Yung-Hsiang Lin, Taipei (TW); Chin-Hsiu Yu, Taipei (TW); Shan-Yu Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/502,102

(22) Filed: Jul. 3, 2019

(65) Prior Publication Data

US 2020/0009207 A1 Jan. 9, 2020

Related U.S. Application Data

(60) Provisional application No. 62/694,497, filed on Jul. 6, 2018.

(30) Foreign Application Priority Data

Jun. 19, 2019 (TW) .............................. 108119809 A

(51) Int. Cl.
  *A61K 36/00* (2006.01)
  *A61K 36/22* (2006.01)
  *A61P 1/16* (2006.01)
  *A61K 31/7024* (2006.01)

(52) U.S. Cl.
  CPC .......... *A61K 36/22* (2013.01); *A61K 31/7024* (2013.01); *A61P 1/16* (2018.01); *A61K 2236/37* (2013.01)

(58) Field of Classification Search
  None
  See application file for complete search history.

(56) References Cited

PUBLICATIONS

Ravani et al, Standardization of processing parameters for the production of ready-to-serve unripe mango beverage (PANA). Journal of Dairying, Foods and Home Sciences (2011), vol. 30, No. 2, pp. 94-98 (Year: 2011).*

* cited by examiner

*Primary Examiner* — Qiuwen Mi
(74) *Attorney, Agent, or Firm* — Chieh-Mei Wang

(57) ABSTRACT

Provided is a method for reducing fat accumulation in and oxidative damage to liver cells by using a green mango extract. Also provided is a method for reducing fat accumulation in liver cells by using compounds of hydrolyzable tannins isolated from the green mango extract.

5 Claims, 12 Drawing Sheets

METHODS TO REDUCE FAT ACCUMULATION AND OXIDATIVE DAMAGE IN LIVER USING GREEN MANGO EXTRACTS AND COMPOUNDS OBTAINED THEREFROM

CROSS-REFERENCE TO RELATED APPLICATION

This application claims priority of U.S. Provisional Application No. 62/694,497, filed on Jul. 6, 2018, and Taiwan patent application No. 108119809, filed on Jun. 19, 2019, the content of which is incorporated herein in its entirety by reference.

BACKGROUND OF THE INVENTION

1. Field of the Invention

The present invention relates to a method for health care by using a green mango extract and hydrolyzable tannins obtained therefrom. Particularly, the present invention relates to a method for reducing fat accumulation and oxidative damage in liver cells by using the green mango extract; and a method for reducing fat accumulation in liver cells by using the hydrolyzable tannins.

2. The Prior Art

The liver is a vital organ in the body responsible for food digestion, energy storage, and detoxification. Fatty liver disease is diagnosed when the liver fat content exceeds 5% of the liver weight. Due to different causes, fatty liver disease is divided into alcoholic fatty liver disease and nonalcoholic fatty liver disease (NAFLD), with the latter being the most common chronic liver disease in the world. NAFLD may be further divided into simple fatty liver and nonalcoholic steatohepatitis (NASH) depending on whether the liver is inflamed. NASH patients have inflammation-induced liver cell damage, which leads to liver fibrosis and may even lead to cirrhosis or liver cancer in severe cases.

Risk factors for NAFLD include obesity, type 2 diabetes, hyperlipidemia, specific drug use, and environmental toxins. Therefore, strategies to prevent or treat NAFLD include reducing caloric intake, increasing exercise, and stopping the use of a particular drug. However, it is not easy for modern people busy with work to follow these lifestyle-changing schedules. In addition, in the field of medicine, no drug is currently available to effectively treat NAFLD. Despite the use of diabetes drugs for NAFLD treatment has been studied, such study is still under exploration.

In order to prevent or reverse fatty liver disease, particularly the NAFLD, and to further reduce the damage to liver cells and liver function, it is necessary to develop a composition that can inhibit fat accumulation and damage in the liver.

SUMMARY OF THE INVENTION

Accordingly, in one aspect, the present invention provides a method for reducing fat accumulation and oxidative damage to a liver cell, including the step of contacting the liver cell with a composition including an effective amount of a green mango extract, wherein the green mango extract is obtained by extraction of a green mango with a solvent; and the green mango is an unripe mango fruit with a length of 3 to 7 cm.

In one embodiment of the present invention, the step of contacting liver cells with a composition including an effective amount of a green mango extract may be accomplished by administering the composition to a human subject orally or parenterally, so that the ingredients of the green mango extract are delivered to the liver cells through blood circulation.

In one embodiment of the present invention, the weight ratio of the solvent to the green mango ranges from 20:1 to 1:1, and the extraction is performed at a temperature between 55° C. and 100° C.

In one embodiment of the present invention, the solvent is water, and composition includes at least 1 mg/mL of the green mango extract.

In one embodiment of the present invention, the oxidative damage to the liver cell that is reduced by the green mango extract includes apoptosis.

In another aspect, the present invention provides a method for reducing fat accumulation in a liver cell, including the step of contacting the liver cell with an effective amount of a compound represented by formula (I):

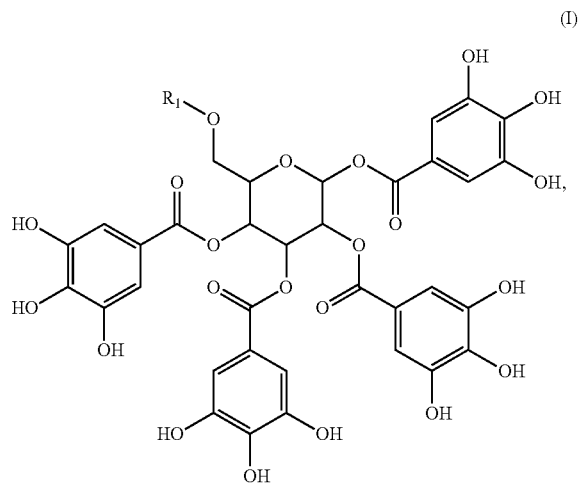

wherein $R_1$ is monohydroxybenzoyl or a polyhydroxybenzoyl.

In one embodiment of the present invention, $R_1$ is monohydroxybenzoyl, such as p-hydroxybenzoyl or m-hydroxybenzoyl. In another embodiment, $R_1$ is polyhydroxybenzoyl, including dihydroxybenzoyl such as 3,4-dihydroxybenzoyloxy, 3,5-dihydroxybenzoyl; and trihydroxybenzoyl such as 3,4,5-trihydroxybenzoyl (i.e., galloyl).

In one embodiment of the present invention, the step of contacting liver cells with an effective amount of a compound of formula (I) may be accomplished by administering an effective amount of the compound to a human subject orally or parenterally, so that the compound is delivered to the liver cells through blood circulation.

In one embodiment of the present invention, the compound of formula (I) is isolated from the aforementioned green mango extract. Not limited to preparation from green mango or other natural sources, this compound may also be prepared by chemical synthesis.

In one embodiment of the present invention, the compound of formula (I) is at a concentration of at least 10 µg/mL.

The present invention discloses that the green mango extract can reduce fat accumulation in and oxidative damage to liver cells, and thus has the potential to decrease the risk of fatty liver disease and to maintain normal liver function. Furthermore, the present invention also discloses a compound of formula (I) which significantly reduces fat accumulation in liver cells. Based on these characteristics, the green mango extracts and the compound disclosed herein can be used to prepare compositions for reducing fat accumulation in and/or oxidative damage to liver cells. The composition may be in the form of powders, granules, solution, gel or paste and may be manufactured as a medicament, food, a drink, or a nutritional supplement that may be administered to a subject orally or via other routes.

The present invention is further explained in the following examples, in reference to the accompanying drawings. It should be understood that the examples given below do not limit the scope of the invention, and that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Definition

Figure 1:
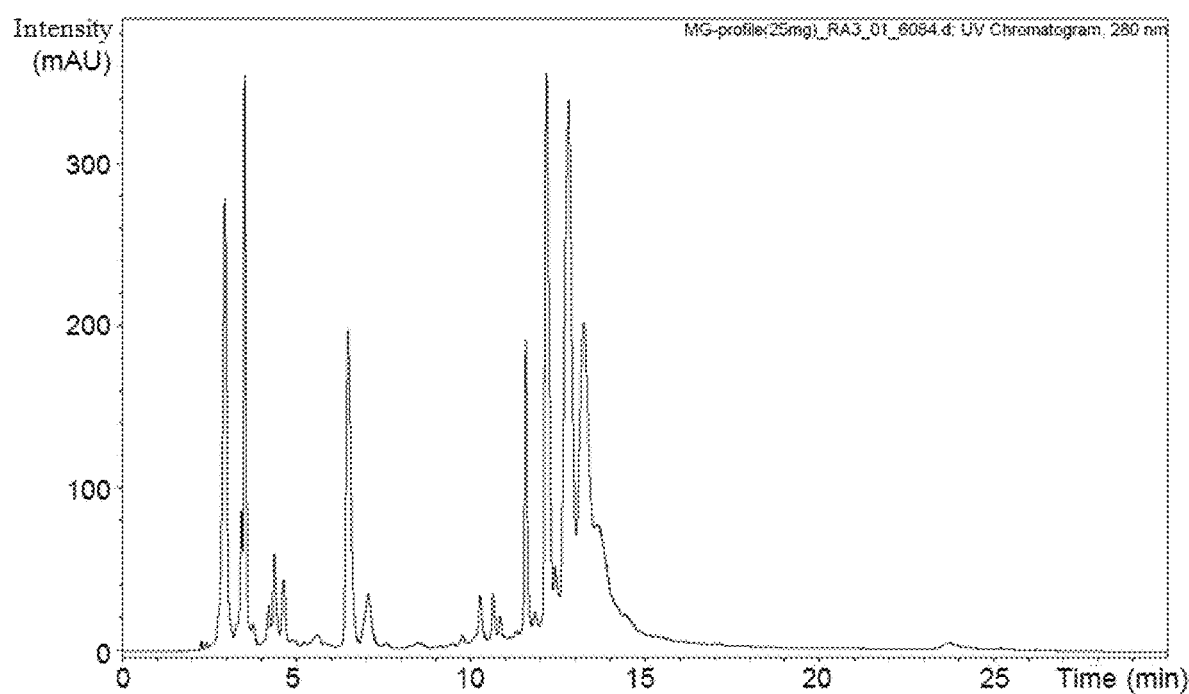
FIG. 1 is a graph of the high performance liquid chromatography (HPLC) fingerprint of a green mango extract according to one embodiment of the present invention.

Unless otherwise specified, "a", "the", and similar terms as used herein shall be interpreted to include the singular and plural.

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The pharmaceutical composition described herein may be formulated, by techniques well known to those skilled in the art, into a dosage form suitable for parenteral or oral administration. The dosage form includes, but not limited to, injection (for example, sterile aqueous solution or dispersion), powders, tablets, troches, lozenges, pills, capsules, dispersible powders, granules, solutions, suspensions, emulsions, syrups, elixirs, slurries, and the like.

The pharmaceutical composition described herein may be administered via parenteral routes including, but not limited to, intraperitoneal injection, subcutaneous injection, intramuscular injection, and intravenous injection.

The pharmaceutical composition described herein may contain a pharmaceutically acceptable carrier that is widely used in the field of pharmaceutical manufacturing. The pharmaceutically acceptable carrier includes one or more agents selected from the group consisting of solvents, emulsifiers, suspending agents, decomposers, binding agents, excipients, stabilizing agents, chelating agents, diluents, gelling agents, preservatives, lubricants, absorption delaying agents, liposomes, and the like. The selection and amount for use of these agents are based on conventional techniques within the profession of those skilled in the art.

The aforementioned pharmaceutically acceptable carrier includes a solvent selected from the group consisting of water, normal saline, phosphate buffered saline (PBS), a sugar-containing solution, an aqueous solution containing alcohol, and combinations thereof.

Materials and Methods

Materials

Dulbecco's modified Eagle's medium (Gibco DMEM), fetal bovine serum (Gibco FBS), penicillin/streptomycin (Gibco), phosphate buffered saline (Gibco PBS) and Hoechst 33342 solution were purchased from Thermo Fisher Scientific. Oil red O and oleic acid were purchased from Sigma. Formaldehyde, isopropanol, and dimethyl sulfoxide (DMSO) were purchased from Echo Chemical. Bovine serum albumin (BSA) was purchased from Bio Basic. Propidium iodide (PI) solution was purchased from BD Biosciences.

Solvents, including n-hexane, ethyl acetate, acetone, methanol, ethanol, acetonitrile, chloroform-$d_1$ (deuteration degree 99.5%), methanol-$d_6$ (deuteration degree 99.5%), heavy water (deuterium oxide, deuteration degree >99.8%), and dimethyl sulfoxide-$d_6$ (deuteration degree >99.9%) were purchased from Merck Taiwan.

Instruments for Chemical Analysis

Compounds are isolated using column chromatography and thin layer chromatography (TLC). Medium pressure liquid chromatography (MPLC) was performed on the CombiFlash® Rf+(Teledyne ISCO) system; and the column medium was selected from Sephadex LH-20 (Amersham Biosciences), Diaion HP-20 (Mitsubishi Chemical), Merck Kieselgel 60 (40-63 μm, Art. 9385), and Merck LiChroprep® RP-18 (40-63 μm, Art. 0250). The high performance liquid chromatography (HPLC) system was equipped with Hitachi L-2310 series pump, Hitachi L-2420 UV-VIS detector (detection wavelength ranging from 200 nm to 380 nm), and D-2000 Elite software for data processing; and the column was selected from analytical columns Discovery® HS $C_{18}$ (250×4.6 mm, 5 m; SUPELCO) and Mightysil RP-18 GP 250 (250×4.6 mm, 5 m; Kanto Chemical), semi-preparative column Discovery® HS $C_{18}$ (250×10.0 mm, 5 m; SUPELCO) and preparative column Discovery® HS $C_{18}$ (250×21.0 mm, 5 m; SUPELCO). The chromatography system was equipped with UV lamp UVP UVGL-25 (wavelength 254 nm and 365 nm). The TLC aluminum plate was coated with the silicone gel 60 $F_{254}$ (0.25 mm; Merck) or RP-18 $F_{254}$s (0.25 mm; Merck).

The chemical structure of compounds was determined by mass spectrometry (MS) and nuclear magnetic resonance spectrometry (NMR). Specifically, tandem mass spectrometer (MS/MS; Bruker amaZon SL system and Thermo Orbitrap Elite system) with two-dimensional ion trap, Fourier transform analyzer, and electrospray ionization (ESI) was employed; and one-dimensional and two-dimensional NMR spectra were obtained by Varian 400 FT-NMR spectrometer operating at 400 MHz, with tetramethylsilane (TMS) as an internal standard (6=0).

Cell Culture

Cells used in the following examples include human hepatoma cell line HepG2 (ATCC HB-8065), which was purchased from the American Type Culture Collection (ATCC). HepG2 cells were cultured at 37° C. under 5% carbon dioxide in DMEM supplemented with 10% FBS and 1% penicillin/streptomycin, hereinafter referred to as DMEM culture medium.

Preparations of Oil Red O Staining Solution and Oleic Acid-BSA Conjugate

To prepare the oil red O staining solution, the dye, oil red O, was first dissolved in 100% isopropanol thoroughly to prepare a 30 mg/mL oil red O stock solution. To obtain a ready-to-use oil red O staining solution, the stock solution was diluted with double deionized water to a concentration of 18 mg/mL and filtered through a 0.22 μm filter immediately before use.

To obtain a DMEM containing oleic acid-BSA conjugate, 10 mg/mL BSA and 28 μg/mL oleic acid were added to a DMEM with 2% FBS and 1% penicillin/streptomycin. The resulting mixture was stirred for about 30 minutes to facilitate the conjugation between oleic acid and BSA and the formation of conjugates.

Oil Red O Staining

The neutral fat content of cells was determined by oil red O staining. Prior to staining, the cells after indicated treatment were washed with PBS and then fixed with 10% formaldehyde for 30 minutes. The fixed cells were washed once with PBS and rinsed with 50% isopropanol for 15 seconds. Thereafter, the cells were stained with the oil red O staining solution for 1 hour. After staining, the cells were washed with PBS and directly examined by microscope (ZEISS Axio Vert. A1). Alternatively, the intracellular dye was dissolved with 100% isopropanol and quantified by spectrophotometry.

Fluorescence Staining

Apoptotic and dead cells were detected by fluorescence staining with Hoechst 33342/PI. The cells after indicated treatment were washed and resuspended with PBS, followed by first addition of PI solution (250 fold dilution) to stain the deoxyribonucleic acid (DNA) of dead cells for 15 to 30 minutes, and subsequent addition of Hoechst 33342 solution (20000 fold dilution) to stain the DNA of all cells for 3 minutes. After staining, the cells were washed with PBS and directly examined by fluorescence microscope. The excitation and detection wavelengths of PI are about 535 nm and 615 nm, respectively. The excitation and detection wavelengths of Hoechst 33342 are about 346 nm and 460 nm, respectively.

Statistical Analysis

Data are expressed as mean±standard deviation (SD). Statistical analysis was performed using Excel software; the statistical significance of the differences between the data was determined by Student's t-test.

EXAMPLE 1

Preparation of the Green Mango Extract

The mango (*Mangifera indica*) described herein refers to the mango cultivars of Taiwan origin, but is not limited thereto. In general, the growth and development of mango fruit is divided into four periods as follows: (1) the young fruit period, at which the fruit begins to grow slowly after the mango flower is thanked and the fruit looks green; (2) the rapid growing period, at which the fruit enlarges fast and the starch in the flesh gradually accumulates; (3) the maturation period, which starts when the endocarp of the fruit hardens; during this period, the fruit appearance does not change much but the weight of the fruit continues to increase, and certain physical and chemical changes are still taking place, for example, the fruit hardness decreases, the sugar content increases, the peel turns yellow, which cause the fruit to ripen completely and become edible; (4) the aging period, which starts when the fruit is completely ripe. The green mango or unripe mango fruit described herein refers to the mango fruit that has not entered the maturation period and the peel has not turned yellow. Since mangos are generally harvested during the maturation period and the aging period, the green mango or unripe mango described herein can also be referred to as "early-harvested mango." The terms "green mango," "unripe mango," and "early-harvested mango" can be used interchangeably.

For preparation of a green mango extract, an unripe mango fruit with a length of about 3 to 7 cm is ground using a homogenizer. Thereafter, the green mango homogenate is extracted by using water, an alcohol, or an alcohol-water mixture as the solvent, to which 0.1% to 5% of a mix of organic acid (such as acetic acid and citric acid) and hydrochloric acid may be added. The weight ratio of the solvent to the green mango homogenate ranges from 20:1 to 1:1. The extraction temperature is between 55° C. and 100° C., preferably between 55° C. and 85° C. In the following Examples 2-4, all the green mango extracts are obtained by extraction of the green mango with an aqueous solution containing 0.1% to 0.5% of acetic acid, citric acid and hydrochloric acid, and the time for extraction is from 0.5 to 3 hours. An HPLC fingerprint as shown in FIG. 1 was obtained when said green mango water extract was subjected to HPLC under the following conditions: the sample was at a concentration of 50 mg/mL and a volume of 20 μL; the column was Mightysil RP-18 GP 250; the mobile phase was water and methanol each containing 0.1% formic acid and mixed according to the gradient program as shown in TABLE 1; the flow rate was 1.0 mL/min; and the detection wavelength was 280 nm.

TABLE 1

| | Time (min) | | | | | | |
|---|---|---|---|---|---|---|---|
| | 0 | 5 | 10 | 20 | 25 | 30 | 30.5 |
| Water | 85% | 85% | 70% | 70% | 0% | 0% | 85% |
| Methanol | 15% | 15% | 30% | 30% | 100% | 100% | 15% |

After the abovementioned extraction, the green mango extract is cooled to room temperature. The extract may be centrifuged at 3,000 to 5,000 rpm for 5 to 10 minutes at room temperature to obtain a supernatant, and the supernatant may be filtered through a 400 mesh filter to remove residual solids. Furthermore, the filtered green mango extract may be concentrated under reduced pressure (less than 1 atm) at 45° C. to 70° C. to obtain a concentrated product. In order to obtain a solid form of green mango extract, the solvent is removed from the concentrated green mango extract by a drying method such as freeze drying, spray drying, or the like, thereby obtaining the powder of green mango extract.

EXAMPLE 2

Reduction of Fat Accumulation in Liver Cells by the Green Mango Extract

In order to examine the effect of the green mango extract on liver fat content, oil red O staining was used to analyze the change in fat content of human hepatoma HepG2 cells treated with the green mango extract described in Example 1. Briefly, HepG2 cells were seeded at 5×10$^5$ cells/well in a 6-well plate, where each well contained 3 mL DMEM culture medium. After cell culture overnight at 37° C., the culture medium was removed, and the cells in each well were treated either with 2 mL DMEM containing 2% FBS or with 2 mL DMEM containing 2% FBS and 1 mg/mL of the green mango extract. After cell culture at 37° C. for 24 hours, the medium was removed, and the cells in each well were treated in the following manner: (a) the cells untreated with the green mango extract were cultured in 2 mL DMEM containing 2% FBS and 1% penicillin/streptomycin (control group); (b) the cells untreated with the green mango extract were cultured in 2 mL of the medium of control group supplemented with oleic acid-BSA conjugate (OA group); or (c) the cells pretreated with the green mango extract were cultured in 2 mL of the medium of control group supplemented with oleic acid-BSA conjugate and 1 mg/mL of the green mango extract (OA+MI group). After cultured at 37° C. for 24 hours, the three groups of cells were washed with PBS and stained with oil red O.

Figure 2A:
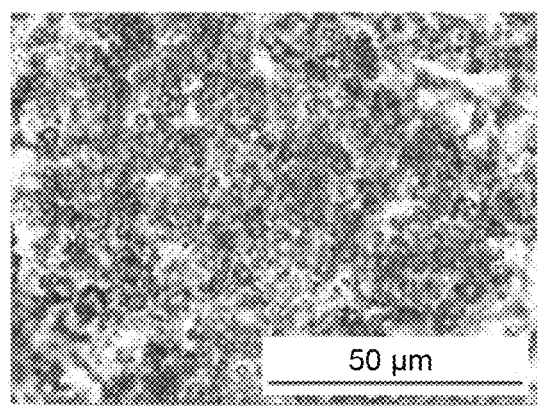
FIG. 2A is a micrograph showing the HepG2 cells treated with oleic acid (OA) alone and then stained with oil red O; the scale bar indicates 50 μm.
Figure 2B:
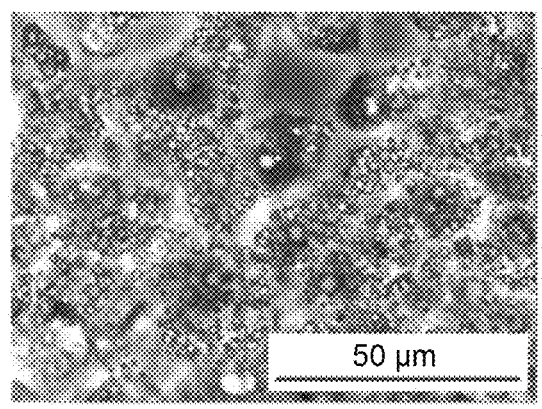
FIG. 2B is a micrograph showing the HepG2 cells treated with oleic acid (OA) and a green mango extract according to one embodiment of the present invention and then stained with oil red O; the scale bar indicates 50 μm.
Figure 2C:
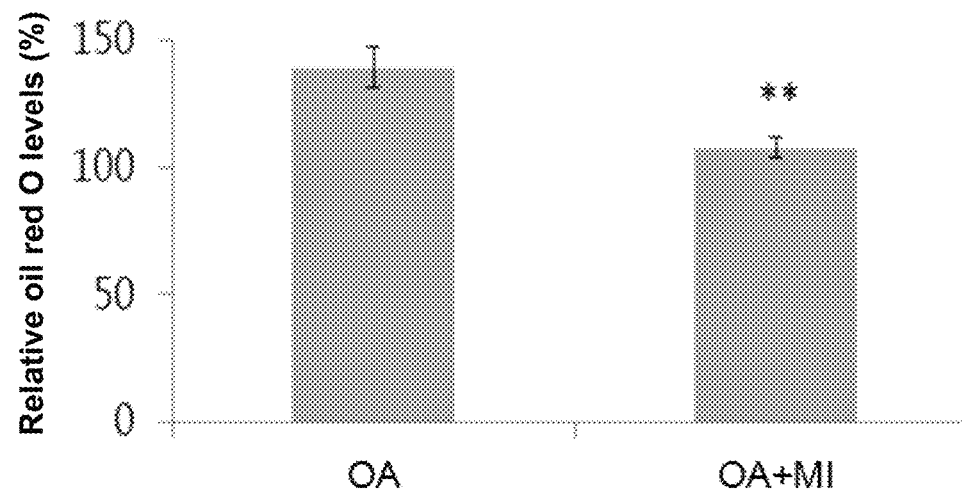
FIG. 2C shows the relative oil red O levels of the HepG2 cells shown in FIG. 2A and FIG. 2B.

FIG. 2A and FIG. 2B show respectively the micrographs of HepG2 cells treated with oleic acid or additionally with the green mango extract and then stained with oil red O. By comparing FIG. 2A with FIG. 2B, it is found that the HepG2 cells treated with oleic acid alone had a large amount of oil droplets stained red; however, the cells additionally treated with the green mango extract were significantly less stained. The oil red O-stained cells were further assayed for dye amount, and the results are shown in FIG. 2C, where the relative oil red O level is expressed as a percentage relative to the oil red O level of the control cells (100%), and ** represents p<0.01 compared with the OA group. According to FIG. 2C, the relative oil red O level or relative fat content of HepG2 cells increased to about 139.6% after treatment solely with oleic acid. In contrast, additional application of the green mango extract significantly reduced the relative oil red O level or relative fat content to about 107.7%. The result indicates that the green mango extract can reduce fat accumulation in liver cells and therefore has the potential to decrease the risk of fatty liver disease.

EXAMPLE 3

Reduction of Oxidative Damage to Liver Cells by the Green Mango Extract

In order to examine whether the green mango extract protects liver cells from oxidative damage, alanine aminotransferase (ALT, also known as GPT) assay and fluorescent staining were used to evaluate cell damage or viability of human hepatoma HepG2 cells pretreated with the green mango extract described in Example 1 followed by treatment with hydrogen peroxide. Briefly, HepG2 cells were seeded at 2×10$^4$ cells/well in a 24-well plate, where each well contained 500 μL DMEM culture medium. After cell culture overnight at 37° C., the culture medium was removed, and the cells in each well were treated either with 200 μL DMEM culture medium or with 200 μL DMEM culture medium containing 1 mg/mL of the green mango extract. After cell culture at 37° C. for 24 hours, the cells were treated in the following manner: (a) the cells untreated with the green mango extract were cultured for 6 hours without hydrogen peroxide stimulation (control group); (b) the cells untreated with the green mango extract were treated with 500 μM hydrogen peroxide for 6 hours ($H_2O_2$ group); or (c) the cells pretreated with the green mango extract were further treated with 500 μM hydrogen peroxide for 6 hours ($H_2O_2$+MI group). Thereafter, each group of cells was subjected to fluorescence staining with Hoechst 33342/PI, or the supernatant from each cell culture was assayed for the ALT levels on an ELISA Reader (BioTek) by using ELISA Kit for Alanine Aminotransferase (USCN SEA207Hu) according to the manufacturer's instructions.

Figure 3:
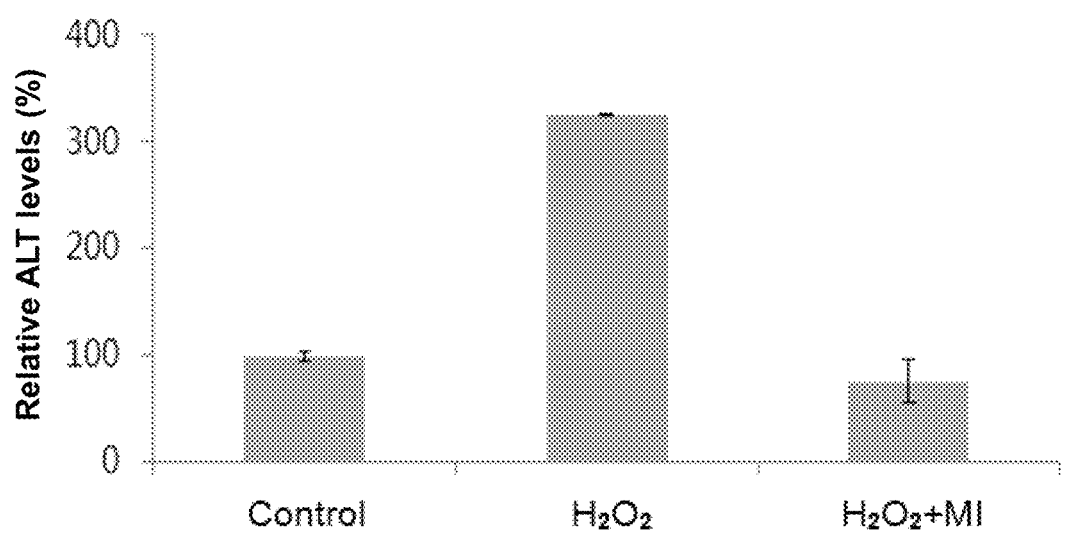
FIG. 3 shows the inhibitory effect of a green mango extract according to one embodiment of the present invention on alanine aminotransferase (ALT) release from the HepG2 cells stimulated with hydrogen peroxide ($H_2O_2$)
Figure 4:
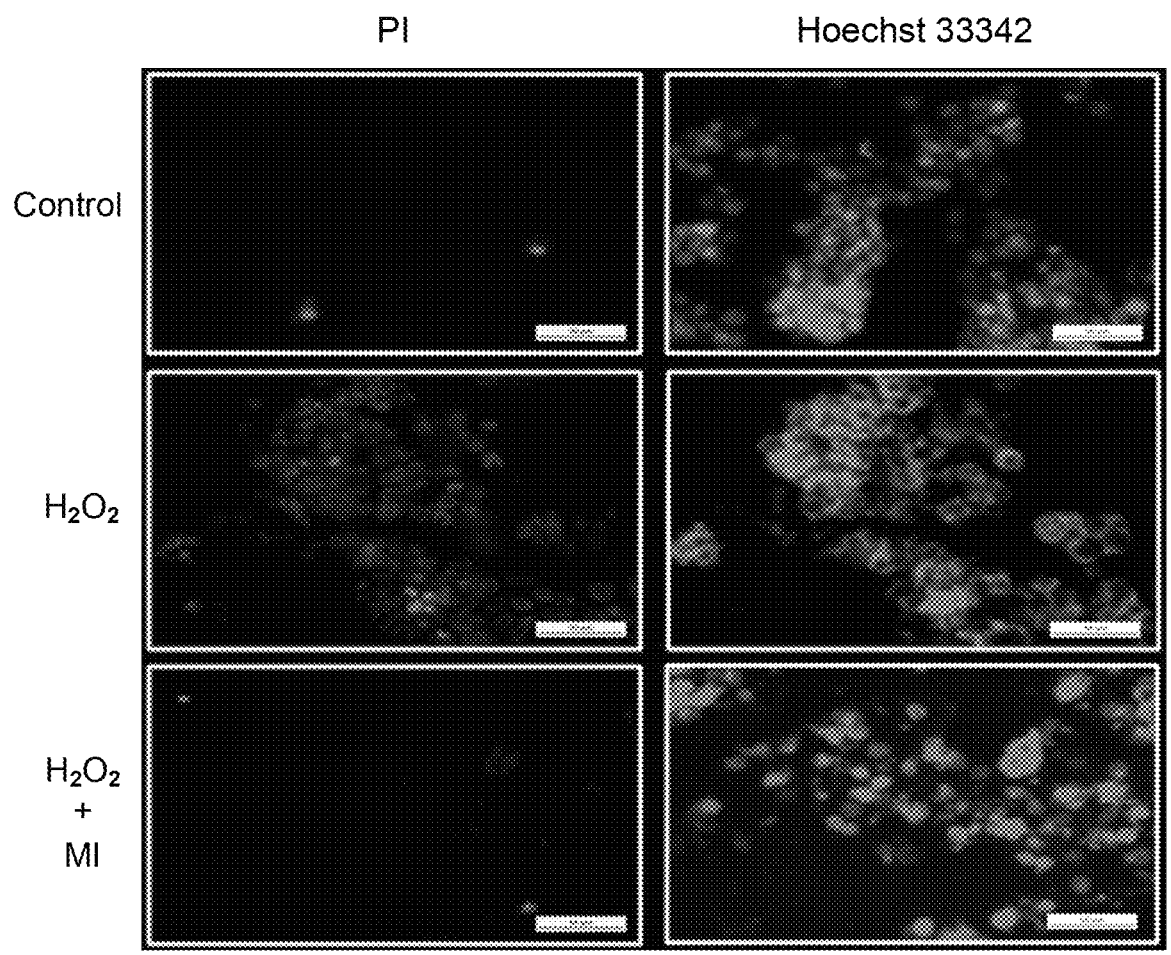
FIG. 4 are micrographs showing Hoechst 33342/PI fluorescence staining of the HepG2 cells treated with hydrogen peroxide ($H_2O_2$) alone, co-treated with hydrogen peroxide and a green mango extract according to one embodiment of the invention, or untreated (control group); the scale bar in each micrograph indicates 50 μm.

FIG. 3 shows the relative ALT levels of the HepG2 cell culture supernatants, which are expressed as a percentage relative to the ALT level of the control cell culture supernatant. According to FIG. 3, when compared with the control group, treatment with hydrogen peroxide induced the production of reactive oxygen species (ROS) in HepG2 cells, leading to cell damage and release of a large amount of ALT, while pre-administration with the green mango extract significantly reduced the cell damage and ALT release. Furthermore, FIG. 4 shows the micrographs of the HepG2 cells fluorescently stained with Hoechst 33342/PI. According to this figure, treatment with hydrogen peroxide increased the PI fluorescence in HepG2 cells compared with the control group, indicating an increase in apoptosis, whereas pre-administration with the green mango extract reduced the PI fluorescence and increased cell viability. These results show that administration with the green mango extract allows liver cells to become resistant to oxidative stress, thereby reducing damage to liver cells and benefiting normal liver function.

EXAMPLE 4

Preparation and Identification of the Compound of Formula (I)

In order to obtain the active ingredients in the green mango extract that reduce fat accumulation in liver cells, firstly, 1 L of the green mango extract was prepared according to the method described in Example 1, and the extract was further extracted three times by liquid-liquid partitioning using ethyl acetate and water at equal proportion. The resulting ethyl acetate fractions were pooled and then concentrated to dryness under reduced pressure to yield about 4.7 g of an ethyl acetate extract. Thereafter, the remaining aqueous fraction was extracted three times by liquid-liquid partitioning using n-butanol and water at equal proportion. The resulting n-butanol fractions and aqueous fractions were pooled, respectively, and then concentrated to dryness under reduced pressure to yield an n-butanol extract and a water extract.

Figure 5:
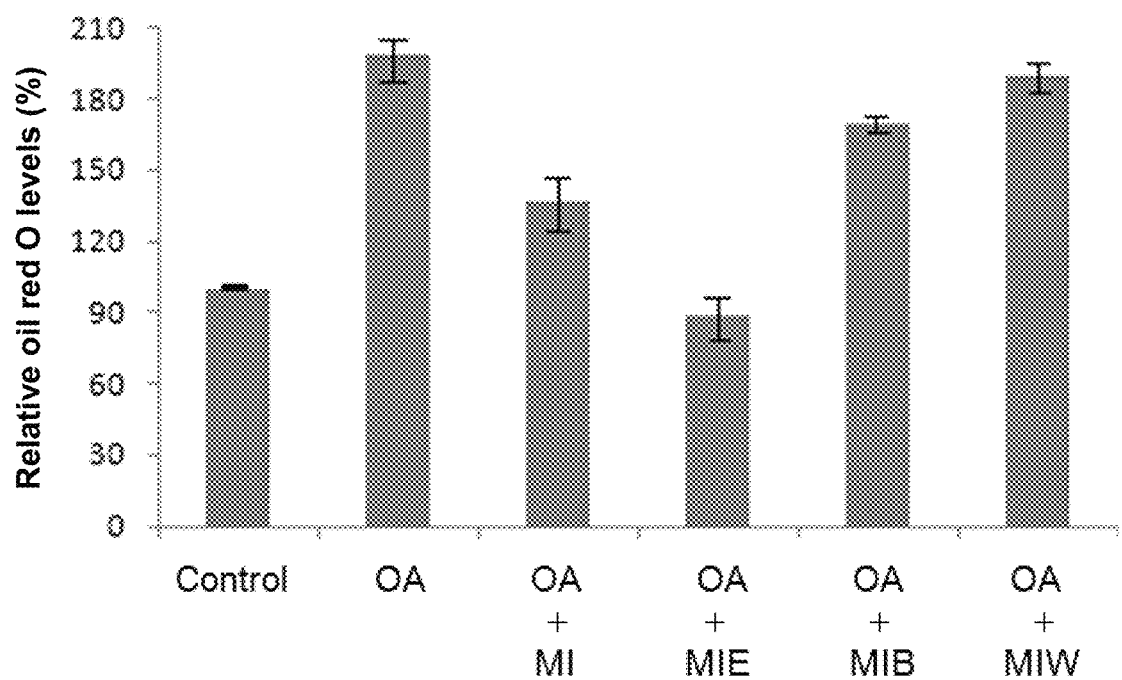
FIG. 5 shows the inhibitory effect of a green mango extract according to one embodiment of the present invention and the secondary extracts therefrom on fat accumulation in oleic acid (OA)-treated HepG2 cells; MI indicates the green mango extract, MIE indicates an ethyl acetate extract, MIB indicates an n-butanol extract, MIW indicates a water extract.

Each of the green mango extract and the secondary extracts therefrom (the ethyl acetate extract, n-butanol extract and water extract) was assayed for the effect on fat accumulation in liver cells, according to procedures similar to those described in Example 2. The results are shown in FIG. 5. According to this figure, the ethyl acetate extract exhibited a more significant inhibitory effect on fat accumulation than the green mango extract. Therefore, the ethyl acetate extract was further fractionated to yield the active ingredients with the fat-reducing activity.

Following bioassay-guided fractionation, the ethyl acetate extract (about 4.7 g) was subjected to Diaion HP-20 column chromatography using mixed water and methanol with decreasing polarity gradient as the eluent, and three fractions (respectively denoted as F1 to F3) were obtained. Thereafter, each of the F2 and F3 fractions was subjected to Sephadex LH-20 column chromatography using a methanol eluent, and each of the eluted solutions was then separated by TLC to obtain three fractions (respectively denoted as F2-1 to F2-3 and F3-1 to F3-3). The F3-2 fraction was further subjected to HPLC (employing a C18 column) using a mixture of water and methanol in a volume ratio of 1:1 as the mobile phase, and finally compound 1 was isolated in an amount of about 13.0 mg. Also, the F2-1 fraction was further subjected to HPLC (employing a C18 column) using a mixture of water and methanol in a volume ratio of 2:1 as the mobile phase, and finally compound 2 was isolated in an amount of about 23.0 mg.

Figure 6:
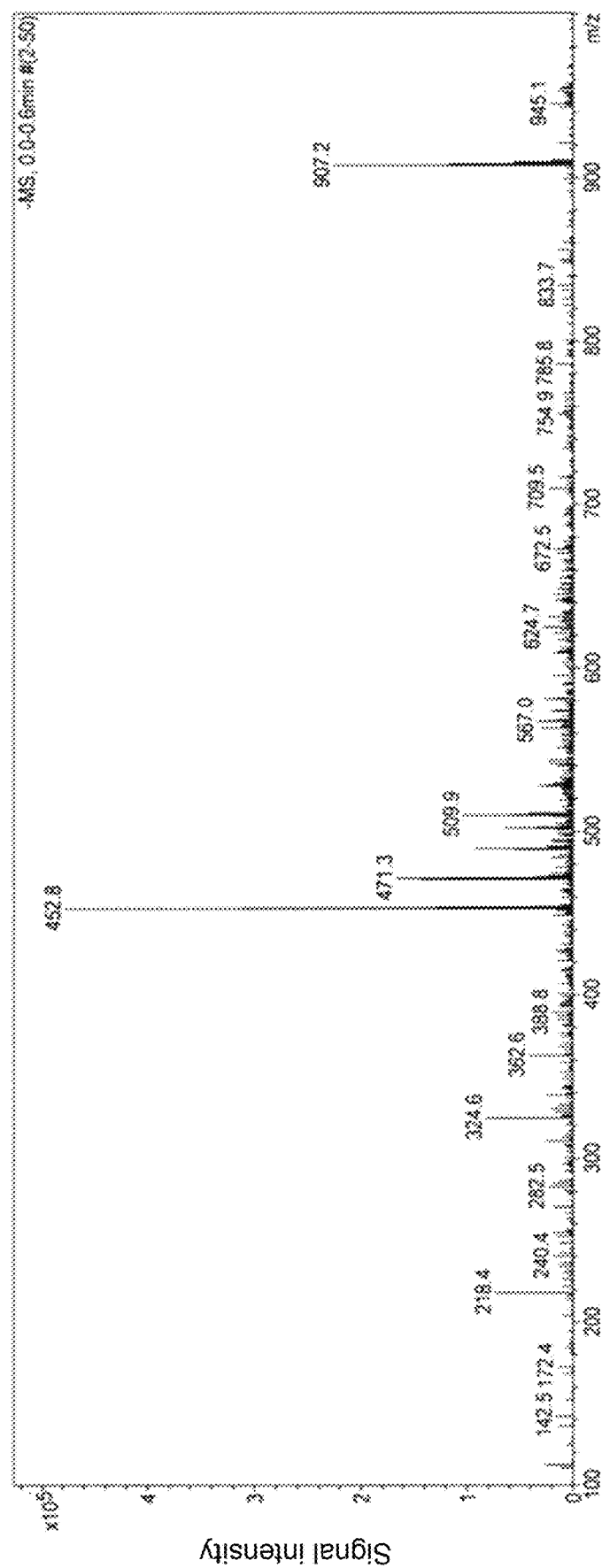
FIG. 6 shows the mass spectrum for compound 1.
Figure 7A:
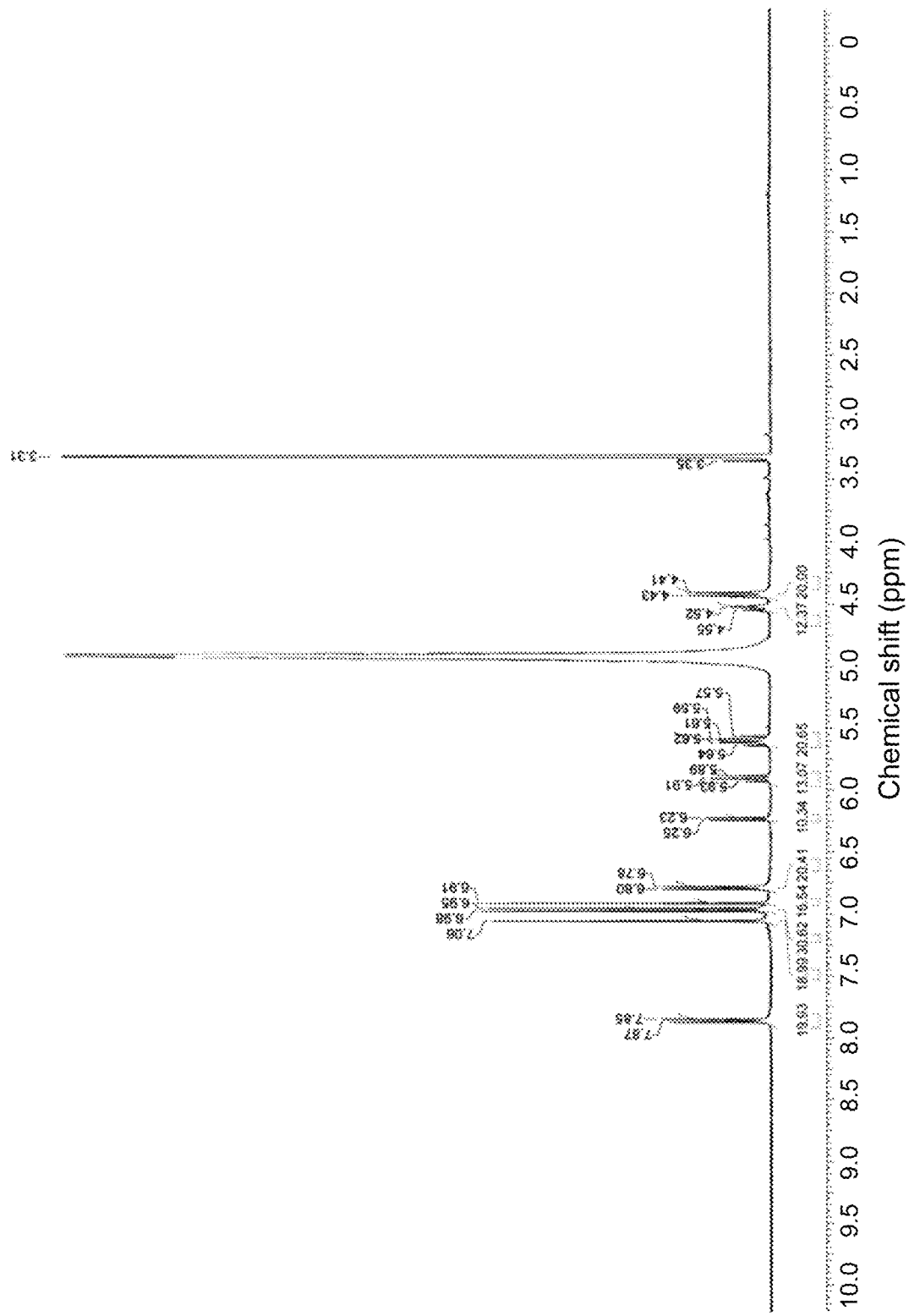
FIG. 7A shows the hydrogen nuclear magnetic resonance ($^1$H-NMR) spectrum for compound 1.
Figure 7B:
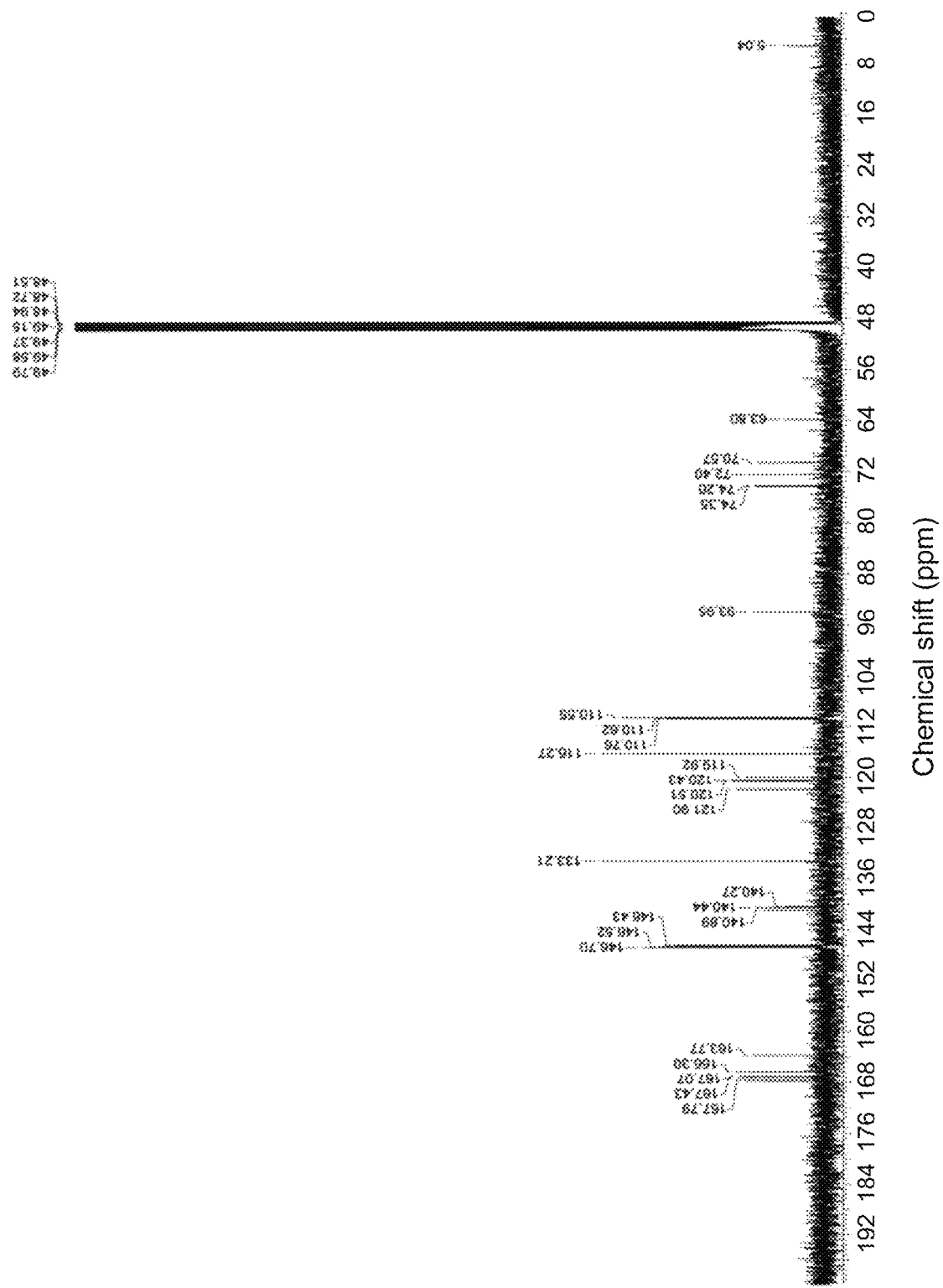
FIG. 7B shows the carbon nuclear magnetic resonance ($^{13}$C-NMR) spectrum for compound 1.
Figure 7C:
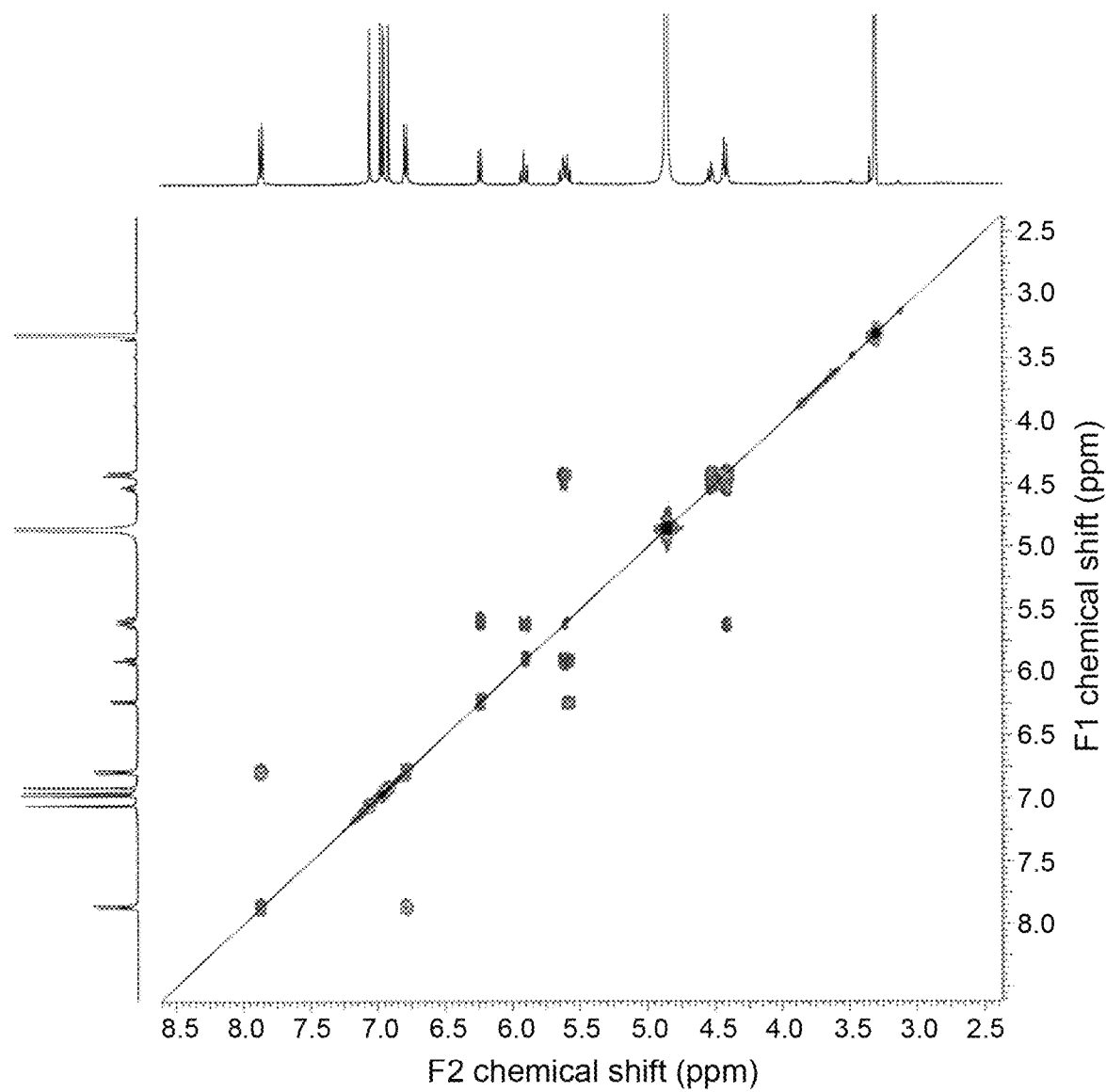
FIG. 7C shows the correlation spectroscopy (COSY) spectrum for compound 1.
Figure 7D:
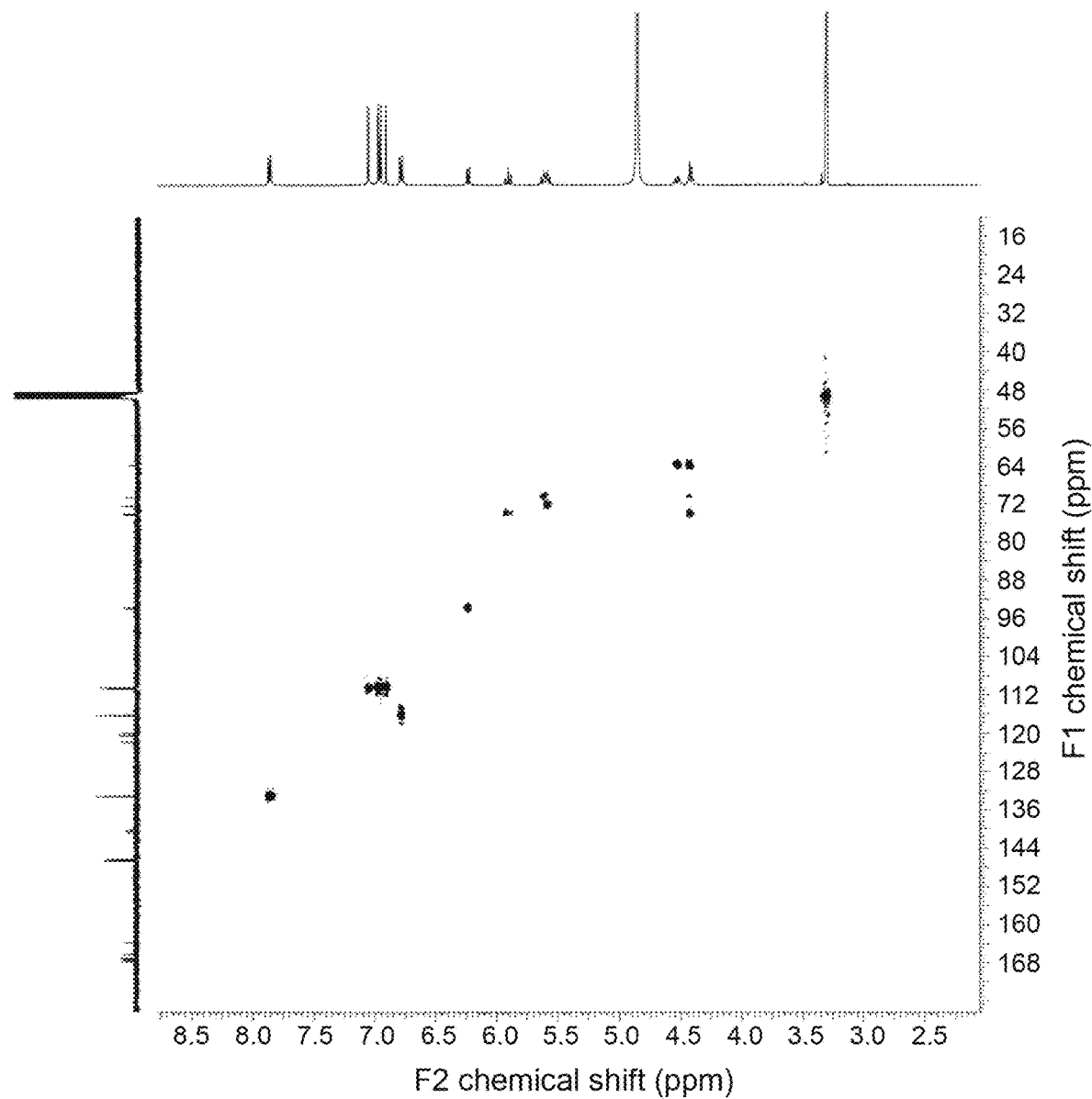
FIG. 7D shows the heteronuclear single quantum correlation (HSQC) spectrum for compound 1.
Figure 7E:
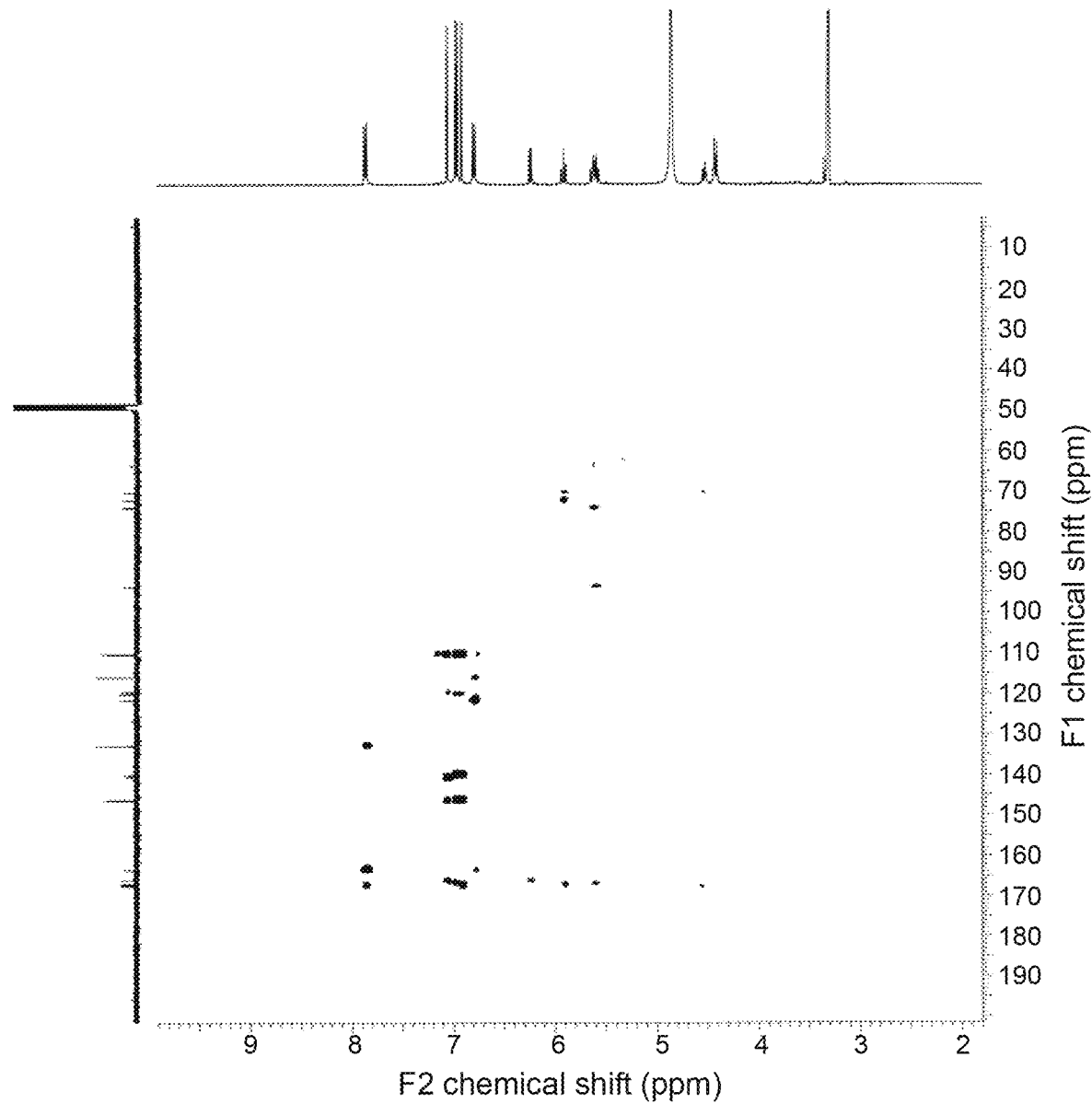
FIG. 7E shows the heteronuclear multiple bond correlation (HMBC) spectrum for compound 1.

The chemical structures of compound 1 and compound 2 were determined by mass spectrometry and nuclear magnetic resonance spectroscopy (NMR). Compound 1 is a light brown oil. From the mass spectrum shown in FIG. 6, a pseudo-molecular ion peak at m/z 907 [M-H]– is observed, so that compound 1 is estimated to have a molecular weight of 908 Da. According to the $^1$H-NMR spectrum shown in FIG. 7A, compound 1 has a main structure composed of a sugar group and five aromatic rings. According to the $^{13}$C-NMR spectrum shown in FIG. 7B, compound 1 has a total of 41 carbon absorption signals, which are 5 carbonyl absorption signals, 5 benzene ring absorption signals, and one set of glycosyl absorption signals. Furthermore, according to the two-dimensional NMR spectra (COSY, HSQC, and HMBC) shown in FIGS. 7C to 7E, the connection between the single sugar group and the five aromatic rings and the position of the substituents in the compound 1 can be inferred. Thus, compound 1 is identified as a hydrolyzable tannin that has not been reported and has the structure represented by formula (Ia). Compound 2 is identified, based on the mass and NMR spectra, as a hydrolyzable tannin having the structure represented by formula (Ib) and the chemical name of 1,2,3,4,6-penta-O-galloyl-glucopyranoside.

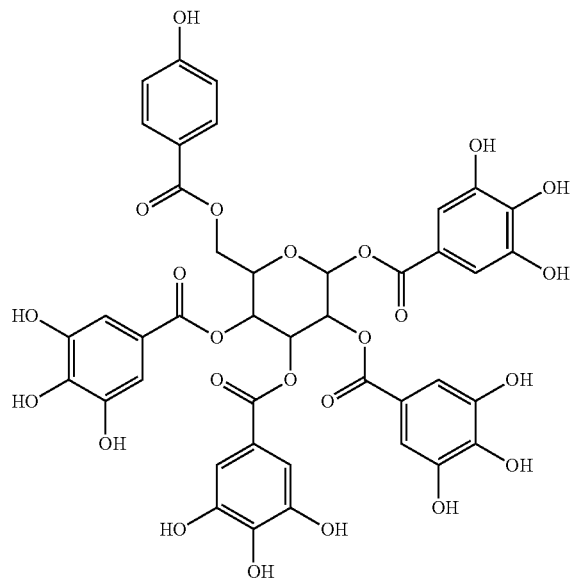

(Ia)

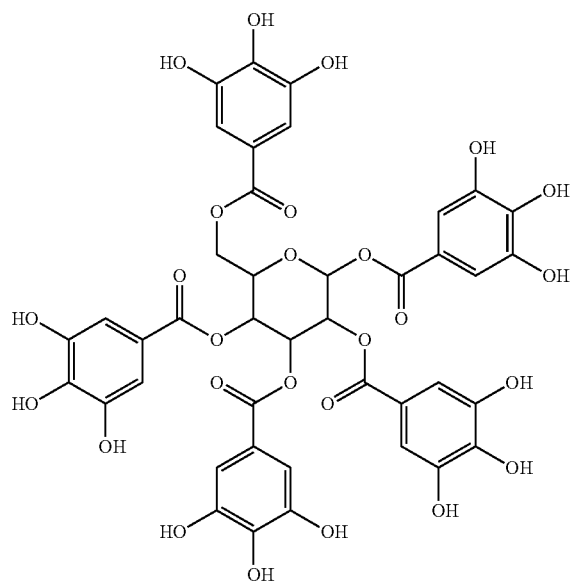

(Ib)

EXAMPLE 5

Reduction of Fat Accumulation in Liver Cells by the Compound of Formula (I)

Figure 8:
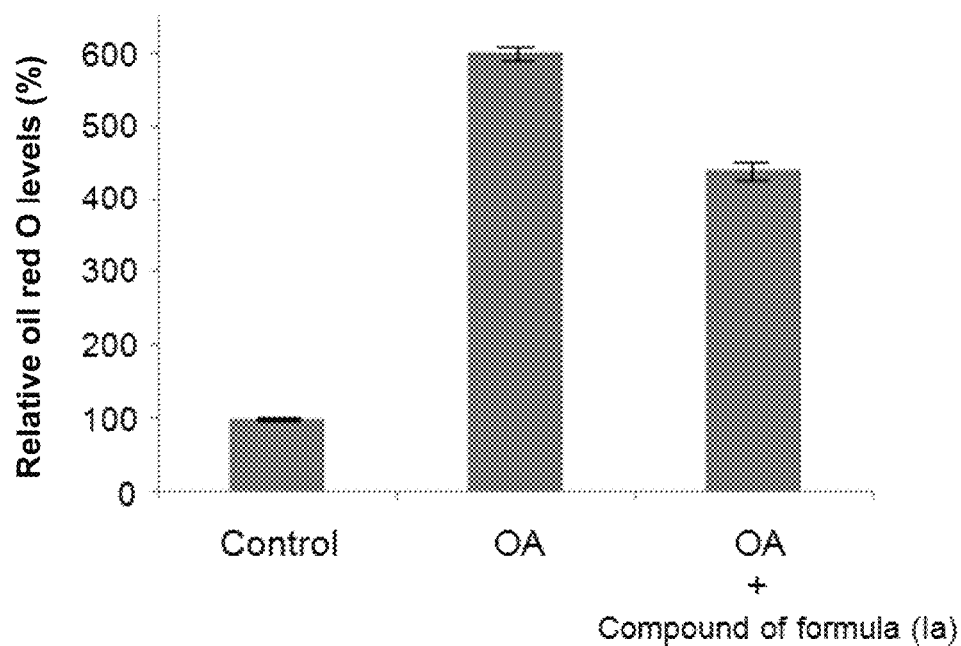
FIG. 8 shows the inhibitory effect of the compound of formula (Ia) on fat accumulation in oleic acid (OA)-treated HepG2 cells.
Figure 9:
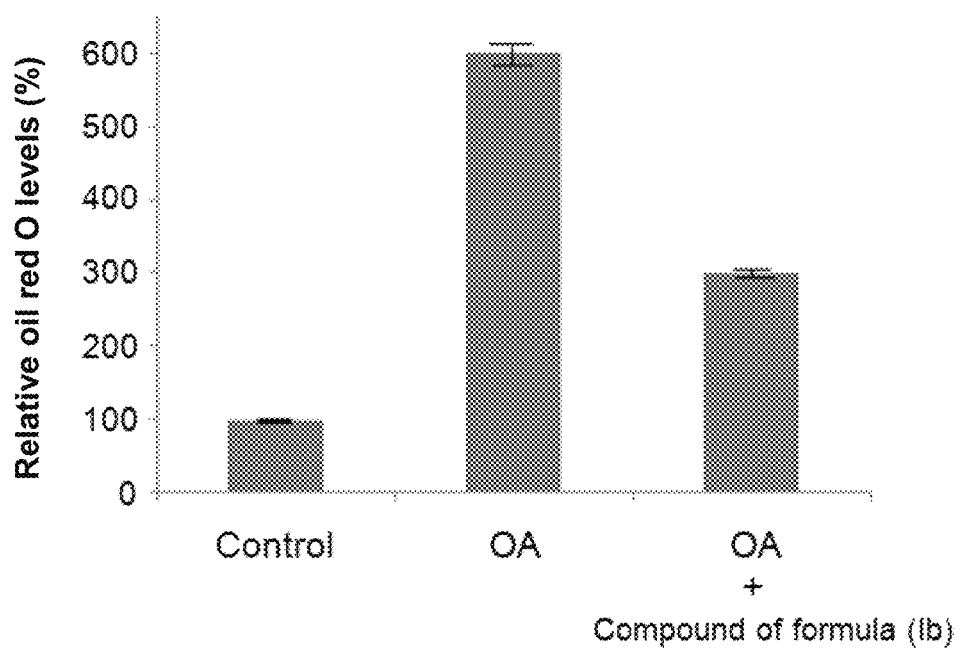
FIG. 9 shows the inhibitory effect of the compound of formula (Ib) on fat accumulation in oleic acid (OA)-treated HepG2 cells.

According to procedures similar to those described in Examples 2 and 3, the compounds of formula (Ia) and (Ib), which were dissolved first in DMSO and then added to the culture medium at a concentration of 10 μg/mL, were assayed for the activity to reduce fat accumulation in liver cells. The results are shown in FIGS. 8 and 9. According to FIGS. 8 and 9, when compared with the treatment with oleic acid alone, additional administration of the compound of formula (Ia) or (Ib) significantly reduced the fat accumulation in HepG2 cells by approximately 33% and 44%, respectively. Because both the compounds of formula (Ia) and (Ib) are compounds of formula (I) as shown below with $R_1$ being p-hydroxybenzoyl and galloyl, respectively, these results show that the compound of formula (I) disclosed herein, wherein $R_1$ is monohydroxybenzoyl or polyhydroxybenzoyl, has the activity to reduce fat accumulation in liver cells and the potential to decrease the risk of fatty liver disease.

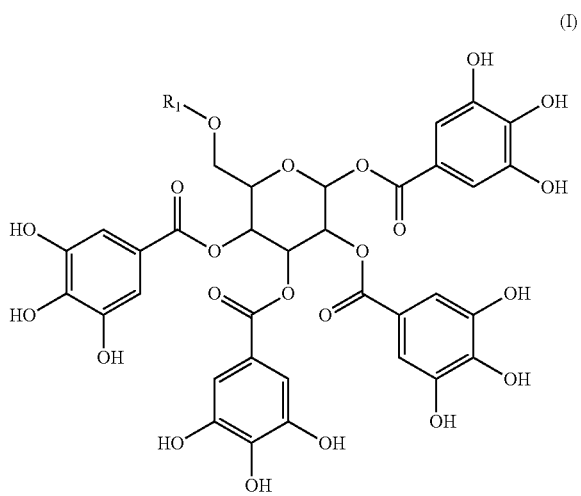

(I)

In conclusion, the present invention discloses that the green mango extract can reduce fat accumulation in and oxidative damage to liver cells, and thus has the potential to decrease the risk of fatty liver disease and to maintain normal liver function. Furthermore, the present invention also discloses a compound of formula (I) which significantly reduces fat accumulation in liver cells. Based on these characteristics, the green mango extracts and the compound disclosed herein can be used to prepare compositions for reducing fat accumulation in and/or oxidative damage to liver cells.

The present invention has been described with reference to the above preferred embodiments. However, it will be apparent to those skilled in the art that modifications and changes in form and detail may be made without departing from the scope of the present invention defined by the appended claims.

What is claimed is:

1. A method for reducing fat accumulation and oxidative damage to a liver cell, comprising the step of contacting the liver cell with a composition comprising an effective amount of an early-harvested mango extract, wherein the early-harvested mango extract is obtained by extraction of an early-harvested mango with a solvent; the early-harvested mango is a mango fruit that has not entered its maturation period; and the effective amount is at least 1 mg/mL.

2. The method of claim 1, wherein the weight ratio of the solvent to the early-harvested mango ranges from 20:1 to 1:1.

3. The method of claim 1, wherein the extraction is performed at a temperature between 55° C. and 100° C.

4. The method of claim 1, wherein the solvent is water.

5. The method of claim 1, wherein the early-harvested mango extract reduces apoptosis of the liver cell.

* * * * *